US005695762A

United States Patent [19]

Berzofsky et al.

[11] Patent Number: 5,695,762

[45] Date of Patent: Dec. 9, 1997

[54] IMMUNODOMINANT SITES OF HTLV-I ENVELOPE PROTEIN

[75] Inventors: Jay A. Berzofsky, Bethesda, Md.; Akihiko Kurata, Nagasaki-ken, Japan

[73] Assignee: The United States of America as represented by the Department of Health and Human Services, Washington, D.C.

[21] Appl. No.: 466,763

[22] Filed: Jun. 6, 1995

Related U.S. Application Data

[63] Continuation of Ser. No. 243,118, May 16, 1994, abandoned, which is a continuation of Ser. No. 401,411, Sep. 1, 1989.

[51] Int. Cl.[6] .......... A61K 39/21

[52] U.S. Cl. .......... 424/188.1; 424/185.1; 424/186.1; 424/187.1; 424/193.1; 424/196.11; 530/324; 530/325; 530/326; 530/327; 530/402; 530/403; 530/806; 530/826

[58] Field of Search .......... 530/326, 325, 530/327, 826, 402, 403, 806, 324; 424/185.1, 186.1, 187.1, 193.1, 188.1, 196.11

[56] References Cited

U.S. PATENT DOCUMENTS

| | | | |
|---|---|---|---|
| 4,525,300 | 6/1985 | Yoshida et al. . | |
| 4,663,436 | 5/1987 | Elder et al. . | |
| 4,689,398 | 8/1987 | Wu et al. . | |
| 4,724,258 | 2/1988 | Yoshida et al. . | |
| 4,822,606 | 4/1989 | Snyderman et al. . | |
| 4,833,071 | 5/1989 | Wang et al. . | |
| 4,879,212 | 11/1989 | Wang et al. . | |
| 5,017,687 | 5/1991 | Vahlne et al. | 530/324 |
| 5,066,579 | 11/1991 | Reyes . | |
| 5,476,765 | 12/1995 | Wang | 435/5 |

OTHER PUBLICATIONS

Townsend et al. "Antigen Recognition by Class I–Restricted T Lymphocytes" in *Annual Review of Immunology*, vol. 7, (1989), edited by Paul et al, published by Annual Reviews Inc. Palo Alto, CA, pp. 601–624. QR180.A5.

Townsend et al. "The Epitopes of Influenza Nucleoprotein Recognized by Cytotoxic T Lymphocytes can be Defined with Short Synthetic Peptides", *Cell*, vol. 44(Mar. 28, 1986), pp. 959–968. QH573.C38.

Tanaka et al., Journal of Immunology, vol. 147, No. 1, pp. 354–360 (1991).

Kiyokawa et al., Proc. Natl. Acad. Sci., USA, vol. 81, pp. 6202–6206 (1984).

Harlow et al., "Antibodies a Lab Manual", Cold Spring, Harbor, New York, pp. 130–132.

Atassi et al., "Antigen Specific T Cell Receptors and Factors," Ed. J.J. Machalonis, CRC Press, Boca Roton, Florida, pp. 7–63.

Palker et al., "Mapping of Immunogen Regions of (HTLV–1) gp 46 and gp21 Envelope with env encoded synthetic peptide and monoclonal antibody to gp46," Journal of Immunology, vol. 142(3), pp. 971–978 (1989).

Malik et al., J. Gen. Vir., vol. 69, pp. 1695–1710 (1988).

Nakamur et al., Int. J. Cancer, vol. 40, pp. 403–407 (1987).

Gazzolo et al., "Direct Activation of Resting T Lymphocytes by Human T–lymphotrophic Virus Type I," Nature, vol. 326, pp. 714–717 (1987).

Harlow et al., "Antibodies: a Laboratory Manual," Cold Spring Harbor, New York, pp. 99 (1988).

*Primary Examiner*—Donald E. Adams
*Assistant Examiner*—Jeffrey Stucker
*Attorney, Agent, or Firm*—Fish & Richardson P.C.

[57] ABSTRACT

The invention resides in various peptides derived from the envelope glycoprotein of HTLV-1 and conjugates of the peptides. Compositions including the peptides are also included in the invention. The peptides, their conjugates and compositions thereof have use in diagnostic and immunization methods, especially those that are based upon T-helper and/or cytotoxic T lymphocyte function.

18 Claims, 4 Drawing Sheets

IMMUNODOMINANT SITES OF HTLV-I ENVELOPE PROTEIN

This application is a continuation application of application Ser. No. 08/243,118, filed on May 16, 1994, now abandoned which in turn is a continuation application of Ser. No. 07/401,411, filed Sep. 1, 1989 and now abandoned. The entire contents of each of these applications is hereby incorporated in entirety by reference.

The sequence of the HTLV-I envelope protein has been known previously. However, the value of using specific epitopes as preferred immunogenic agents for use in eliciting immune response as shown herein is new. Compositions containing VIE1, VIE8/SP4a, and VIE10 as preferred antigens which can be administered as immunogens is new.

BRIEF DESCRIPTION OF THE INVENTION

HTLV-I (Human T-cell lymphotropic virus type 1) is the retrovirus causally related to adult T-cell leukemia/lymphoma and also associated with a neurological disorder, tropical spastic paraparesis or HTLV-I-associated myelopathy. The development of these two different diseases among HTLV-I infected individuals may depend in part on differences in their T-cell immunity associated with a difference of HLA phenotype. Peptides corresponding to 17 sites in the HTLV-I envelope protein were tested for their antigenicity for lymph node cells from B10.BR, B10.D2, B10.A(5R), and B10.HTT congenic mice, representing four independent MHC haplotypes, immunized with the native envelope protein. Ten of the 17 tested sites were predicted to be amphipathic α-helical sites and all of them were found to be antigenic for at least one of the four MHC congenial strains of mice. Three of the 17 sites were amphipathic $3_{10}$-helical sites and four sites were predicted to be non-helical sites: none of the $3_{10}$-helical sites were antigenic and only one of four non-predicted sites was found to be immunodominant. Furthermore, three potent immunodominant peptides, V1E1 (342-363), V1E8/SP4a (191-209), and V1E10 (141-156) were also shown to be immunogenic; i.e., these peptides could be used to immunize mice to elicit proliferative responses of lymph node cells to the native HTLV-I envelope protein. Furthermore, these three peptides were able to prime animals for an enhanced antibody response to the native protein. Because this priming followed the same Ir gene control as the proliferative response, it probably reflects the ability of these peptides to prime helper T cells. The localization of immunodominant sites in HTLV-I envelope protein in mice may be useful for finding antigenic and immunogenic sites in humans, for developing a peptide vaccine for the virus, and possibly for aiding in prognosis for the development of different disease manifestations of HTLV-I infection.

BACKGROUND OF THE INVENTION

The human T-cell lymphotropic virus type 1 (HTLV-I) was the first retrovirus shown to be causally related to a specific human malignancy, adult T-cell leukemia/lymphoma (ATLL) (Poiesz, et. al. Proc. Natl. Acad. Sci. U.S.A. 77.7415–7419., Yoshida, M., I. Miyoshi, and Y. Hinuma, et. al. Proc. Natl. Acad. Sci. U.S.A. 79:2031–2035). Recently it was found that the same virus was also associated with a chronic myelopathy in the tropics and in southwestern Japan, HTLV-I-associated tropical spastic paraparesis (HTLV-I/TSP) (Johnson, et. al. Ann. Neurol 21:113–116. Gessain, et. al. Lancet 2:407–410., Rodgers-Johnson et. al. Lancet 2:1247–1248., Vernant, et. al. Ann.

Neurol 21:123–130.) or HTLV-I-associated myelopathy (HAM) (Osame, et. al. Lancet 1:103 1–1032.) The development of these two different diseases in HTLV-I infected individuals may depend in part on differences in the nature of patient T-cell responses to HTLV-I because there is some indication of an HLA phenotype-association with the risk of ATLL and TSP/HAM among HTLV-I seropositive individuals, (Usuku et. al. Ann. Neurol 23:S143–S150. This HLA association of neurologic manifestations of HTLV-I infection can be correlated with a difference in lymphocyte proliferative response to the virus, namely, a high response in TSP/HAM and low response in ATLL. For these reasons, it was important to identify epitopes of HTLV-I recognized by T cells, in order to begin to test the hypothesis that T-cell responses to different HTLV-I epitopes might result in either protective immunity or autoimmune disease. Because of the difficulty of testing a large number of potential epitopes in patients, we have chosen to first identify potent T-cell epitopes in mice. Experience from influenza (Lamb, et. al. Nature 300:66–69., Hurwitz I. Immunol 133:3371–3377,) HIV, (Cease et. al. Proc. Natl. Acad. Sci. U.S.A. 84:4249–4253., Berzofsky et. al. Nature 334:706–708) and malaria (Good et. al. Science 235:1059–1062., Good et. al. Procl Natl. Acad. Sci. U.S.A. 85:1199–1203., Dontfraid et. al Mol. Biol. Med., Sinigaglia et. al Nature 336:778–780) indicate a good correlation between epitopes recognized by murine T cells and those recognized by human T cells.

DeLisi and Berzofsky (Delisi et. al. Proc. Natl. Acad. Sci. U.S.A. 82:7048–7052) analysed the sequences of immunodominant sites of protein antigens and found that most of the T-cell epitopes corresponded to regions that could fold as amphipathic helices. An improved computer algorithm "AMPHI" was developed for the prediction of amphipathic helical structures in proteins (Margalit et. al. J. Immunol. 138:2213–2229) and applied to the prediction of immunodominant helper T-cell sites in the HIV-1 envelope protein (Cease et. al. Proc. Natl. Acad. Sci. U.S.A. 84:4249–4253) and *Plasmodium falciparum* malaria circumsporozoite protein (Good et. al. Science 235:1059–1062., Good et. al. Proc. Natl. Acad. Sci. U.S.A. 85:1199–1203).

FIGURE LEGENDS

FIG. 1. Location and predicted conformation of synthetic peptides. Row A shows the predicted amphipathic α-helical sites (solid bars) and $3_{10}$-helical sites (hatched bars). Based on the prediction, the peptides (V1E1-10) in line B were synthesized. The line C shows the location of another series of peptides (SP1-11)[24]; these sites are relatively hydrophilic sites in the HTLV1 envelope protein. V1E8 and SP5 are completely included in SP4a and V1E9, respectively. Also, V1E7 and Sp2, V1E4 and SP8, and V1E5 and SP10 partially overlap.

FIG. 2. Proliferative responses of native envelope protein-immune lymph node cells of B10.BR (upper panel) and B10.A(5R) (lower panel) mice to the immunogen and the synthetic peptides recognized by at least one of the tested strains: V1E1 (▲), V1E2 (Δ), and VIE9 (□)for B10.BR, V1E8 (●) for B10.BR and B10.A(5R), and V1E10 (○) for B10.A(5R) ("NP" experiments described in the text). Responses to PPD (■) are also shown. HTLV1 envelope protein-immune lymph node cells ($4\times10^5$/well) were cultured with various concentration of peptides for 5 days and the cultures were pulsed with 1 μCi of [$^3$H]-TdR for the last 16 h. Results are expressed as Δ geometric mean (cpm)× SEM. Control cultures without antigen gave 2,548 cpm for B10.BR and 3,394 cpm for B10.A(5R).

FIG. 3. Responses of peptide-immune lymph node cells to the native envelope protein ("PN" experiments described in the text) and potent antigenic peptides. The left column shows the response of B10.BR lymph node cells immunized with peptides, V1E1 (top), V1E8 (middle), and V1E10 (bottom), to native envelope protein (●), V1E1 (▲), V1E8 (○), V1E10 (□) and PPD (■). The middle and right vertical columns show the responses of B10.D2 and B10.A(5R) mice, respectively. The data are shown as Δ geometric mean (cpm)×SEM. The no-antigen backgrounds were: B10.BR, 11,743 cpm (V1E1), 5,280 cpm (V1E8), and 7,855 cpm (V1E10); B10.D2, 9,437 cpm (V1E1), 3,121 cpm (V1E8), and 7,340 cpm (V1E10); B10.A(5R), 10,205 cpm (V1E1), 2956 cpm (V1E8), and 5,395 cpm (V1E10).

FIG. 4. Ability of peptide preimmunization to enhance the antibody response to native HTLV-I envelope glycoprotein. Five mice per experimental group of each strain CB10.BR, upper panel, and B10.A(5R), lower panel) were preimmunized i.p. with 10 nmoles of the indicated peptide in CFA, or PBS in CFA as a control, and 15 days later were boosted with 5.6 μg of affinity purified envelope protein in IFA. Bleeds were taken before the peptide immunization and at the indicated times after the immunization with whole protein. Antibodies from individual animals were assayed in duplicate for binding to whole affinity-purified envelope protein as described in Materials and Methods. The geometric mean titer for each group of five animals is plotted, with geometric standard error of the mean.

MATERIALS AND METHODS

Mice. B10.D2 (I-$A^d$, I-$E^d$), B10.BR (I-$A^k$, I-$E^k$) and B10.A (5R) (I-$A^b$, I-$E_\beta{}^b$ $E_\alpha{}^k$) mice were obtained from the Jackson Laboratory (Bar Harbor, Me.). B10.S (9R) (I-$A^s$, I-$E_\beta{}^s$ $E_\alpha{}^k$) and B10.HTT (I-$A^s$, I-$E_\alpha{}^s$ $E_\beta{}^k$) mice were bred in our facility.

Purified viral protein. The HTLV-I envelope protein was obtained from a Triton X-100 lysate of HTLV-I-infected HUT-102 cells using an affinity column made with purified IgG from an HTLV-I seropositive subject as described [19].

Sequence analysis of HTLV-I envelope protein and prediction of T-cell antigenic sites. Polypeptide segments segments with helical amphipathicity, that is, segments which, if helical, would have hydrophilic residues on one face and hydrophobic residues on the opposite face, are predicted to be frequently immunodominant sites in protein antigens seen by T-helper cells and cytotoxic T-cells [17,18,20–22]. The helical amphipathicity of the HTLV-I envelope protein was analysed with a computer algorithm, AMPHI, and 15 potential sites were identified as shown in FIG. 1. Hydrophilic regions of HTLV-I gp46 and p21 were identified by the method of Kyte and Doolittle [23].

Peptide synthesis. Two series of HTLV-I envelope peptides were prepared independently under two different strategies (Table 1). In one series, eight peptides based on the prediction of helical amphipathicity (V1E1, V1E2, V1E3, V1E4, V1E5, V1E6, V1E7, V1E8, and V1E9) and one non-predicted control peptide (V1E10) were synthesized. For the other series, 10 peptides (SP1–6,SP8–11) were synthesized on a Dupont 2100 solid phase peptide synthesizer [24] based upon the high hydrophilicity of sequence without analysing their conformation, originally, in order to search for B-cell epitopes [24]. The V1E series of peptides were synthesized on an Applied Biosystem 430 A peptide synthesizer by using the solid phase peptide synthesis method [25,26] and cleaved from the resin by hydrogen fluoride (HF). The low/high HF method [26] was employed for peptide V1E9 to remove the formyl protecting group from tryptophan and the standard high HF method was used for the other peptides. The peptides were purified by gel filtration on a Biogel P4 column in 9% formic acid. In the case of the peptides V1E9 and V1E10, for which we detected a spontaneous stimulatory effect even after Bio-gel purification, further purification was performed by preparative reverse phase HPLC.

Immune lymph node cell proliferation assay. Mice were immunized with either 0.1 nmole of purified envelope protein or 3 nmol of peptide in 50 μl of complete Freund's adjuvant (Difco) subcutaneously at the base of the tail. Eight days later, a single cell suspension of the draining lymph nodes was prepared and the cells were plated in quadriplicate at 3 or $4\times10^5$/0.2 ml in flat-bottomed Costar 96-well plates in complete medium with or without antigens as described [27]. The cultures were pulsed with 1 μCi of [$^3$H] TdR (6.7 Ci/mmol; New England Nuclear, Boston, Mass.) for the last 16 hr of a 5-day culture and incorporated [$^3$H] was estimated by β-emission spectroscopy.

Immunization for antibody responses. Mice were prebled and then immunized i.p. with 10 nmoles of a given peptide in CFA or with PBS in CFA, bled 14 days later, and boosted on day 15 with 5.6 μg of affinity purified envelope protein in IFA. Bleeds were taken at weekly intervals thereafter.

Antibody solid-phase radioimmunoassay. Antibody to whole HTLV-I envelope protein was measured by solid-phase radiobinding assay as described [24]. Briefly, Immulon 2 microtiter plates (Dynatech) were coated with affinity purified protein, prepared as described above, in sodium carbonate buffer, pH 9.6 overnight at 4° C., then washed, blocked with 5% nonfat dry milk in coating buffer for 2 hr at 4° C., and washed with PBS containing 0.5% Tween 20, 3% nonfat dry milk, and 0.1% azide. Sera from individual mice were serially diluted and each dilution was incubated in duplicate webs coated with antigen for 1 h at 23° C. Wells were washed three times and developed with a 45-min incubation with 50 μl of a 1/200 dilution of rabbit anti-mouse IgG (BCA/Cappel Products, West Chester, Pa.), followed by a wash and a 30-min incubation with $10^5$ cpm/well of $^{125}$I protein A. Each plate had negative and positive controls consisting of anti-gp46 monoclonal antibody 1C11 or control P3x63 ascites fluid each diluted 1/50. Titers were determined as the greatest dilution still giving twice the background cpm binding.

DETAILED DESCRIPTION OF THE INVENTION

It is the purpose of this invention to provide immunogenic peptides for use as vaccines to elicit T-cell immunity against HTLV-I. It is a further purpose of the invention to provide peptides for use in priming antibody response against pathogenic proteins of the HTLV-I virus as treatment for already-infected individuals.

Peptides of the invention are also useful as diagnostic agents to evaluate patient T-cell responses. The particular peptides taught herein may be conjugated to each other or to other moieties to specifically generate desired responses in the patient. Examples of such moieties are B cell epitopes to produce neutralizing antibodies and cytotoxic T-cell epitopes to induce cytotoxic T-cells.

The information relating to sequences disclosed indicates that individual mouse phenotypes respond with varying specificity to different immunogens in the same manner that individual human response varies. However, it is known that peptide epitopes which elicit T-cell responses in mice also elicit immune responses in humans. (See references 9–16 in the list of references.) As in mice, different phenotypes may vary somewhat in response to a given epitope. Therefore, preferred vaccines contain more than one immunogenic dominant epitope.

Two independent series of HTLV-I envelope peptides were synthesised in two laboratories, based on two different strategies. One set was chosen based on prediction of amphipathic helical conformation to look for T-cell epitopes, and the other set was made originally to search for B-cell epitopes, and so had been chosen on the basis of hydrophilicity of amino acid sequence. The antigenicity of these peptides was tested on native HTLV-I envelope protein-immunized murine lymph node cells and strong antigenicity was predominantly detected in peptides predicted to be amphipathic, α-helical sites. Furthermore, three antigenic peptides could be used to immunize mice to elicit T-cells proliferating in response to the native envelope protein, and to prime helper T-cells for an enhanced antibody response to the native envelope protein. These antigenic and/or immunogenic peptides identified in the murine system should be helpful for analysing the difference in immune responses to HTLV-I among patients with TSP/HAM and ATLL and their healthy seropositive relatives and also maybe useful for developing a peptide vaccine protecting against HTLV-I transmission and HTLV-I-associated disease development.

Figure 1:
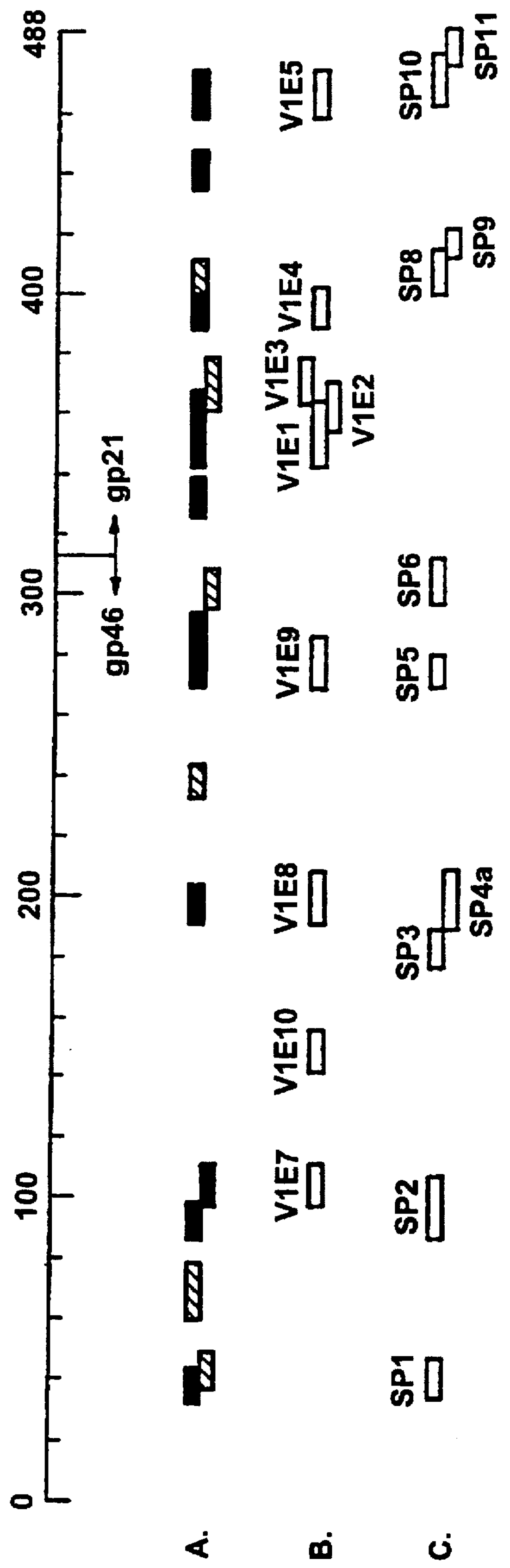

The computer algorithm, AMPHI, was used for identifying predicted T-cell sites, based on segments with potential amphipathic helical structure, in the HTLV-I-envelope protein whose primary amino acid sequence was identified by Seiki et al. [28]. The algorithm identified 15 predicted sites; nine of them were amphipathic α-helical sites and 5 of them were $3_{10}$-helical sites as shown in FIG. 1A. In one predicted site, 387-411, α-helicity changes to $3_{10}$-helical character in the C-terminal half. One series of peptides, V1E1–5 and V1E7–9, were synthesized, based on the analysis, and V1E10 was synthesized as a control peptide with non-predicted sequence (FIG. 1B). Although another series of peptides, SP1–6 and SP8–11, were synthesized independent of these predictions, 7 of 10 peptides (SP1, SP2, SP4a, SP5, SP8, SP9, and SP10) corresponded to either α or $3_{10}$ predicted sites coincidentally. Furthermore, complete sharing or partial overlap of amino acid sequence was observed between some of the peptides in the two series: SP4a (190-209) and V1E9 (268-286) included V1E8 (191-209) and SP5 (269-280), respectively and V1E7 and SP2, V1E4 and SP8 , and V1E5 and SP 10 overlapped partially (FIG. 1B, 1C, and Table 1).

Figure 2:
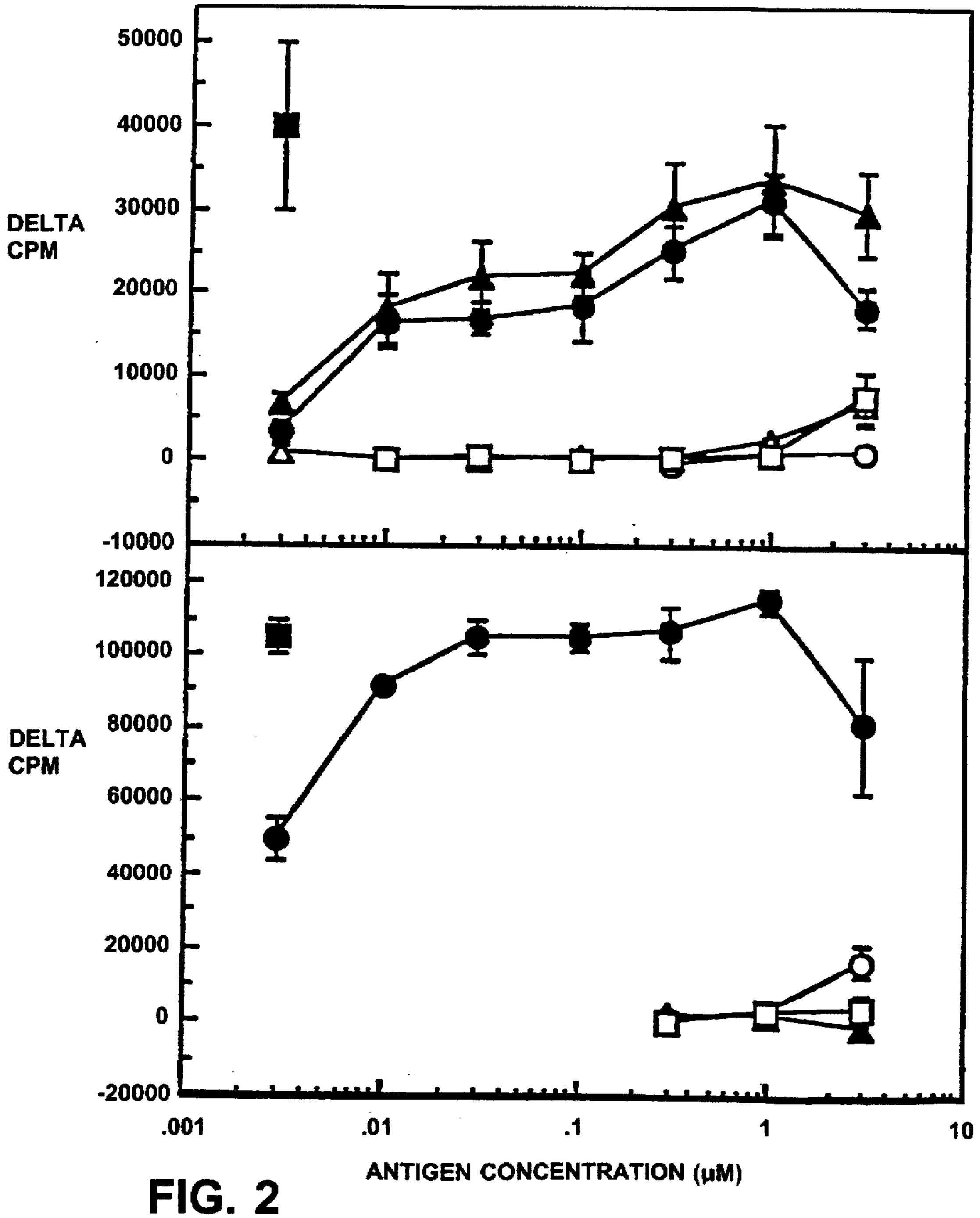

Identification of sites after immunization with native HTLV-I envelope protein. Table 2 shows the proliferative response of HTLV-I envelope protein-immune lymph node cells to the synthetic peptides. Congenic mice representing four independent MHC types were studied. Moreover, these strains differ only in their MHC region. Peptides V1E8 and SP4a induced prominant proliferative responses of B10.BR and B10.A(5R) lymph node cells and V1E1 elicited remarkable response only in B10.BR mice. These two sites, V1E8/SP4a and V1E1, were potent antigenic sites in HTLV-I envelope protein and elicited proliferative response in these strains of mice even at 0.01 μM of antigen concentration (FIG. 2.). V1E2 and V1E9 were also antigenic in envelope-immune B10.BR mice and V1E10 in B10.A(5R) mice (Table 2), but these were much less potent on a molar basis in dose-response curves (FIG. 2). No site was identified for B10.D2 and B10.HTT (and B10.S(9R)) mice that was as highly antigenic as V1E1 and V1E8/SP4a for B10.BR and B10.A(5R) mice. However, SP1, SP5, SP10, V1E5, and V1E9 were immunodominant for B10.HTT and SP1, SP2, SP4a, SP5, V1E4, V1E7, V1E9, and V1E10 were for B10.D2 as shown in Table 2. The responses of B10.S(9R) mice were the same as those of B10.HTT (data not shown). The fact that SP4a, but not V1E8 which is contained within SP4a, stimulated B10.D2 envelope-immune T cells suggests that the determinant seen by H-$2^d$ mice is slightly different from that seen by the other strains that respond to both peptides, and requires the additional $NH_2$-terminal leucine residue present in SP4a but not in V1E8. Interestingly, all of these antigenic sites, except for V1E10, were amphipathic α-helical portions of the HTLV-I envelope and no amphipathic $3_{10}$-helical site was involved, as summarised in Table 3.

Figure 3:
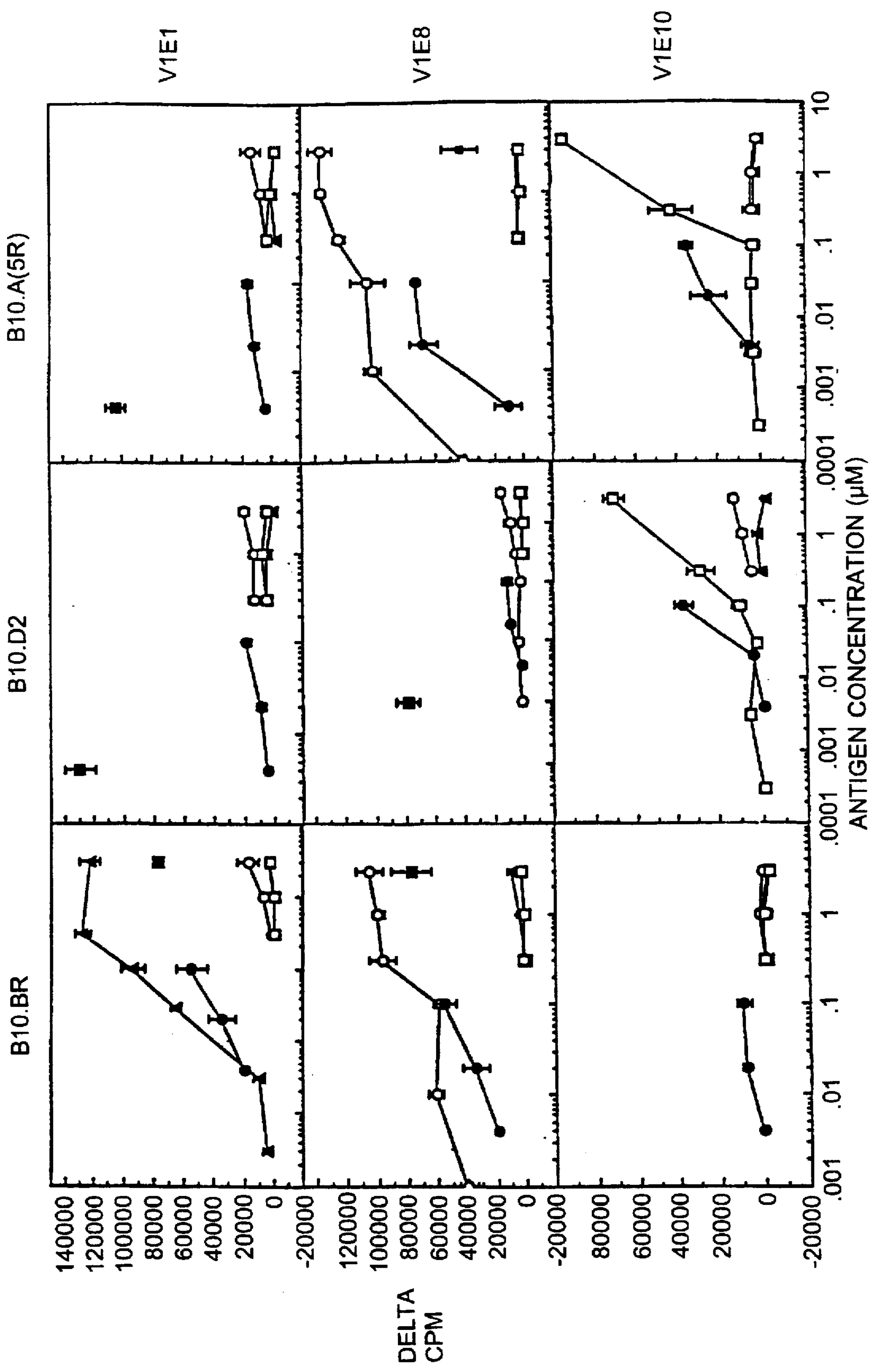

Responses to native envelope after immunization with peptides. For developing a peptide-vaccine, the candidate peptide should have the capability to elicit in vivo a T cell response to the whole native molecule from which the peptide derives. The peptides, V1E1, V1E8, and V1E10, were found to be immunodominant sites by the results of the above experiments in which the native envelope protein was used as immunogen and synthetic peptides were used as antigens in secondary in vitro culture (a native immunogen/peptide test antigen or "NP" experiment). Therefore B10.BR, B10.D2, and B10.A(5R) mice were immunized with these three peptides individually and tested the response of peptide-immune lymph node cells to the native envelope protein (a peptide immunogen/native test antigen or "PN" experiment). As shown in FIG. 3, the peptide V1E8, antigenic in B10.BR and B10.A(5R) in the NP direction, could immunize mice to elicit the response of lymph node cells to the native envelope protein as well as the immunogen (V1E8) itself in the same strains of mice. Likewise, the peptides V1E1 and V1E10, antigenic in B10.BR and B10.D2, respectively, in the NP experiments, were also immunogenic in the corresponding strains of mice for eliciting T cells responding to the native protein in PN experiments (FIG. 3). The concentrations of the secondary antigens producing the maximum responses in these PN experiments were similar for the peptide immunogens and the native protein antigen, the HTLV-I envelope protein.

Figure 4:
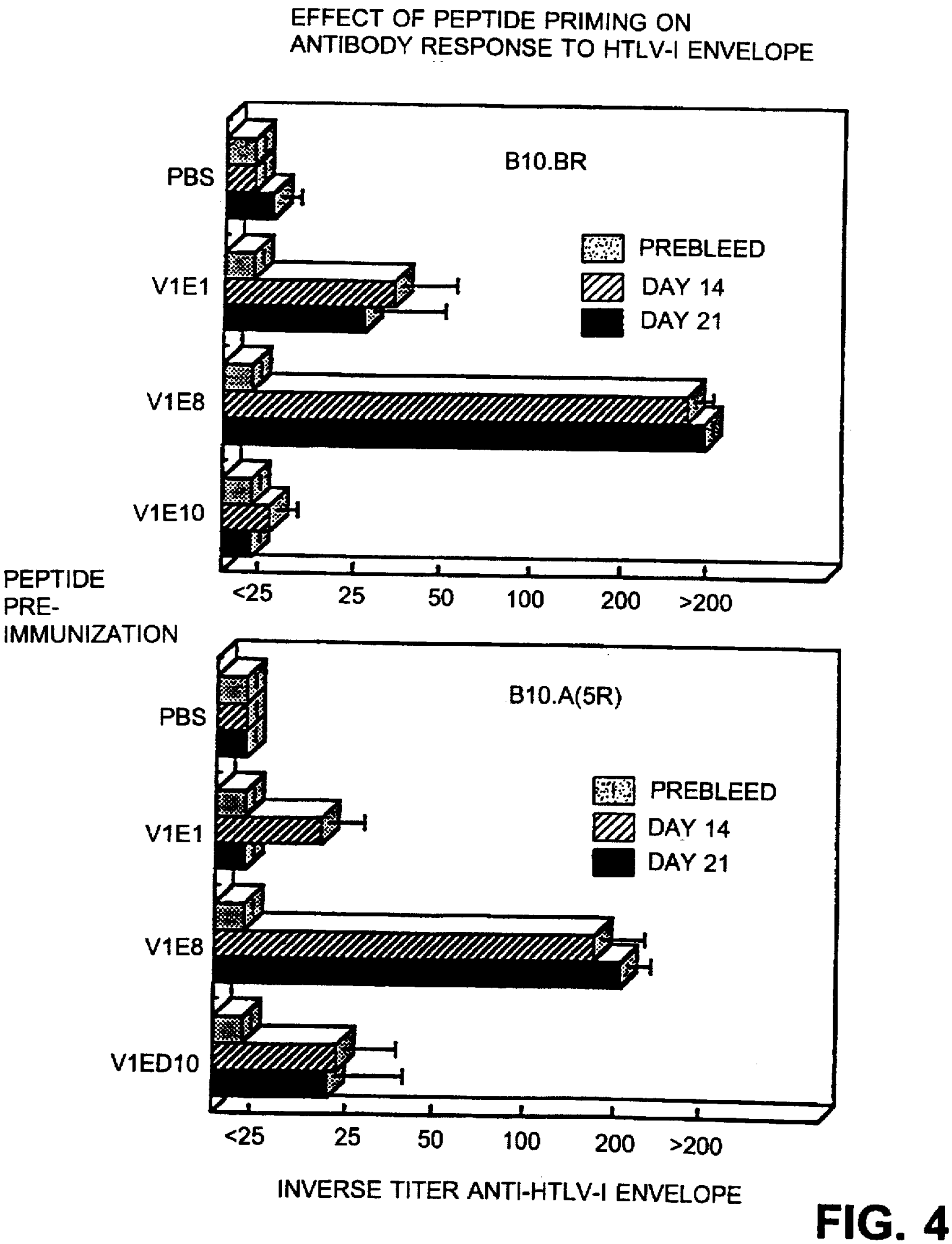

Ability of peptides to prime helper T cells for antibody responses to the whole envelope protein. In order to assess whether the peptides that could prime mice for a T-cell proliferative response to the native protein could also prime helper T cells for an enhanced antibody response to the whole envelope protein, four groups of five mice each of two strains were immunized first i.p. with 10 nmoles, of one of three peptides (without any carrier) or PBS as a control in CFA. Fifteen days later, the mice were boosted i.p. with a suboptimal dose of 5.6 μg of affinity-purified envelope protein in IFA, and bled on days 14 and 21 after the boost. Antibodies were measured to the affinity-purified envelope protein by radiobinding assay as described in Materials and Methods. Mice preimmunized with only PBS uniformly failed to produce any measurable binding activity (FIG. 4), consistent with the suboptimal immunization with whole protein. In B10.BR mice, preimmunization with peptide V1E8 and to a lesser extent with peptide V1E1, both of which are immunogenic in this strain, produced significant titers of antibodies binding the envelope protein. In contrast, preimmunization with peptide V1E10 failed to enhance the antibody response in B10.BR mice which also do not manifest a proliferative response to this peptide. In B10.A (5R) mice, which give a proliferative response to peptides V1E8 and V1E10 but not V1E1, an enhanced antibody response to the envelope protein was observed in those mice immunized with V1E8 and V1E10, and a weaker response on day 14 but not day 21 in those immunized with V1E1. Thus, the enhancement of antibody responses followed the same genetic Ir gene control as the T-cell proliferative response. Therefore, these data were interpreted as reflecting the priming of helper T cells so that a secondary response occurs when the mice are first immunized with whole protein. We noted the presence of some anti-HTLV-I envelope antibodies in the mice immunized with peptides two weeks earlier, but before they were boosted with whole protein (data not shown). No antibodies were found in PBS-immune mice. This result suggests that the peptides may also contain B-cell epitopes. In particular, peptide SP4a, which coincides with V1E8, has been shown to be a B-cell epitope in humans (Palker et. al. J. Immunol. 142:971-1-978). However, even if some priming of B cells occurs, such priming of B cells by uncoupled small peptides without a carrier implies that these peptides contain effective helper T-cell determinants. Thus, in any case, the results of immunization with uncoupled peptide and the Ir gene control of the antibody response parallel to that of the T-cell proliferative response indicate that the three peptides tested can induce T-cell help as well as T-cell proliferation.

The overlap of amino acid sequences useful as immunogens and as antibody primers has been observed in several cases, possibly due to the relatively high hydrophilic character of some amphipathic helical segments. However, as disclosed herein, hydrophilicity of amino acid sequence of peptides is not significantly correlated with the immunodominance of peptides for proliferative T-cell responses (J. L. Spouge, H. R. Guy, and J. A. Berzofsky, unpublished observations). In fact, one of the two most potent immunodominant sites, V1E1 in gp21, was not identified by the algorithm that selected peptide sequences because of their high hydrophilicity. Hence, the Preneficial peptides are not obvious in view of prior trackings in the art.

Table 3A shows the relation between immunodominance and the potential amphipathicity of the HTLV-I envelope peptides. Interestingly, ten of the eleven immunodominant sites (all except for V1E10) were amphipathic α-helical sites and no amphipathic $3_{10}$-helical sites were identified as immunodominant. Only one of four non-helical sites were immunodominant. The conformation of $3_{10}$-helices is energetically less stable than that of α-helices and usually short pieces of $3_{10}$-helix tend to be at the N- and C-termini of α-helices. Although the original study (Margalit et. al. J. Immunol. 138:2213-2229) of published immunodominant sites did not detect a difference in antigenicity between amphipathic α-helices and $3_{10}$-helices, P. Hale et al. (manuscript submitted) recently found that amphipathic $3_{10}$-helical sites in the HIV envelope protein were rarely immunogenic as compared to the high tendency toward immunodominance of the amphipathic α-helical sites. It is noteworthy that the difference in antigenicity between amphipathic α-helices and $3_{10}$-helices is revealed in the envelope protein of two human retroviruses. The efficacy of the prediction of amphipathic α-helical segments as immunodominant sites in HTLV-I envelope protein is demonstrated in Table 3B. Of 11 sites found to be immnunogenic, 10 sites were segments predicted to amphipathic α-helices. Furthermore, no site predicted to be an amphipathic α-helical site is among the 6 sites found to be non-immunogenic.

The proliferative responses of native envelope protein-immunized lymph node cells to the synthetic peptides were clearly dependent on the MHC haplotype. Four congenic strains of mice were used, differing only in their MHC type. They represent eight different I-A and I-E class II MHC molecules. Sites 190-209 (V1E8/SP4a) and 342-363 (V1E1) were found to be especially potent sites in the HTLV-I envelope protein: the responses of B10.BR and B10.A(5R) mice to V1E8/SP4a and of B10.BR mice to V1E1 occurred even at the low concentration of 0.01 μM in NP experiments. Although the maximum response of envelope protein-immune lymph node cells was not different among the four congenic strains of mice, B10.BR, B10.D2, B10.A(5R), and B10.HTT, no site was identified to be so potent at low concentrations for B10.D2 and B10.HTT mice as V1E1 and V1E8/SP4a were for B10.BR and B10.A(5R) mice. It was also found that three of the epitope peptides of the HTLV-I envelope (V1E8/SP4A, V1E1, and V1E10) primed mice for memory T cell help to enhance antibody responses to B-cell epitopes of the envelope protein.

Asymptomatic seropositive carriers of HTLV-I and patients with ATLL and TSP/HAM have comparable anti-HTLV-I antibody titers in their sera. In contrast, a difference in HLA haplotype and in lymphocyte proliferative response to HTLV-I virions among the patients with these two distinct diseases was reported from southwestern Japan, an endemic area for HTLV-I (Usuku et. al. Ann. Neurol 23:S143-S150). The patients with HAM were high responders to HTLV-I virions in peripheral blood lymphocyte (PBL) cultures in vitro, whereas ATLL patients were low responders in their analysis. Moreover, this difference in lymphocyte response was correlated to the difference in HLA haplotype: healthy HTLV-I carriers with HAM-associated HLA haplotypes tended to show higher HTLV-I-specific lymphocyte responses than healthy carriers with HLA haplotypes correlated with development of ATLL. When the response of human PBL to the synthetic HTLV-I peptides identified in the current study is analysed, it should be possible to detect more distinct MHC-associated differences in the T-cell responses among the carriers and patients with ATLL and HAM because individual peptide epitopes should show clearer genetic restriction than the whole envelope protein, as shown here in mice. Also, responses to particular peptides may be associated with the diseases TSP/HAM, especially if these diseases have autoimmune mechanisms.

Recently, Palker et al. (J. Immunol. 142:971-978) reported that the central region of HTLV-I gp46 envelope glycoprotein defined by synthetic peptide SP4A (residues 190-209) bound antibodies from 78% of HTLV-I seropositive humans. Thus, the SP4A/V1E8 region contains an immunodominant T-cell site in mice of three of four MHC types tested (current study) and also a major B-cell epitope in man. While sites of B and T cell recognition frequently differ in location within a protein and in structural and sequence features (Berzofsky et. al. Immunol. Rev. 98:9–52), major T- and B-cell sites can coincide within the same molecule (Takahashi et. al. Proc. Natl. Acad. Sci. U.S.A. 85:3105–3109., Thomas et. al. Eur. J. Immunol. 17:133–136., Palker et. al. J. Immunol. 142: in press).

As the incidence of disease among HTLV-I infection is low compared with AIDS virus infection, it is difficult to test a vaccine for HTLV-I even if it is developed. However, this observation also suggests that in HTLV-I infection, the immune system is working more effectively for protection against the development of the diseases than in AIDS virus infection.

TABLE 1

Sequence of synthetic HTLV1 envelope peptides

| PEPTIDES | NUMBER OF AMINO ACIDS | AMINO ACID SEQUENCE* |
|---|---|---|
| SP1 (SEQ ID NO.:1) | 33–47 | VSSYHSKPCNPAQPV |
| SP2 (SEQ ID NO.:2) | 86–107 | (C)PHWTKKPNRNGGGYYSASYSDP |
| SP3 (SEQ ID NO.:3) | 176–189 | (C)LNTEPSQLPPTAPP(Y) |
| SP4a (SEQ ID NO.:4) | 190–209 | (C)LLPHSNLDHILEPSIPWKSK(Y) |
| SP5 (SEQ ID NO.:5) | 269–280 | (Y)LPFNWTHCFDPQ(C) |

TABLE 1-continued

Sequence of synthetic HTLV1 envelope peptides

| PEPTIDES | NUMBER OF AMINO ACIDS | AMINO ACID SEQUENCE* |
|---|---|---|
| SP6 (SEQ ID NO.:6) | 296–312 | (C)PPFSLSPVPTLGSRSRR |
| SP8 (SEQ ID NO.:7) | 400–415 | CRFPNITNSHVPILQE |
| SP9 (SEQ ID NO.:8) | 411–422 | (C)PILQERPPLENR |
| SP10 (SEQ ID NO.9) | 462–480 | CILRQLRHLPSRVRYPHYS |
| SP11 (SEQ ID NO.:10) | 477–488 | (C)RYPRYSLIKPESSL |
| V1E1 (SEQ ID NO.:11) | 342–363 | SGKSLLHEVDKDISQLTQAIVK |
| V1E2 (SEQ ID NO.:12) | 353–370 | DISQLTQAIVKNHKNLLK |
| V1E3 (SEQ ID NO.:13) | 362–378 | VKNHKNLLKIAQYAAQN |
| V1E4 (SEQ ID NO.:14) | 388–402 | EQGGLCKALQEQCRF |
| V1E5 (SEQ ID NO.:15) | 458–475 | LAGPCILRQLRHLPSRVR |
| V1E7 (SEQ ID NO.:16) | 97–111 | GGYYSASYSDPCSLK |
| V1E8 (SEQ ID NO.:17) | 191–209 | LPHSNLDHILEPSIPWKSK |
| V1E9 (SEQ ID NO.:18) | 268–286 | TLPFNWTHCFDPQIQAIVS |
| V1E10 (SEQ ID NO.:19) | 141–156 | FTQEVSRLNINLHFSK |

*Amino acids in parentheses have been added to peptides to facilitate coupling to carrier protein (C) and iodination of peptide (Y) for another study [24]. These residues in parentheses are not present in the predicted amino acid sequence of HTLV-I envelope glycoprotein reported by Seiki et al. [28].

TABLE 2

The proliferative response of HTLV1 envelope protein-immunized lymph node cells to the synthetic peptides and the immunogen

| | B10.BR | | B10.D2 | | B10.A(5R) | | B10.HTT | |
|---|---|---|---|---|---|---|---|---|
| Antigens | ΔCPM (SEM) | S.I. | ΔCPM (SEM) | S.I. | ΔCPM (SEM) | S.I. | ΔCPM (SEM) | S.I. |
| SP1 | −2,792 (1.05) | 0.57 | 16,121 (1.19) | 2.99 | −1,886 (1.34) | 0.52 | 11,919 (1.22) | 5.15 |
| SP2 | 686 (1.13) | 1.11 | 23,724 (1.21) | 3.93 | −106 (1.37) | 0.97 | *5,008 (1.18) | 2.74 |
| SP3 | 359 (1.14) | 1.06 | *11,148 (1.32) | 2.38 | −1,405 (1.08) | 0.64 | 2,733 (1.13) | 1.95 |
| SP4a | 26,184 (1.16) | 5.04 | 17,561 (1.18) | 3.17 | 34,607 (1.08) | 7.50 | 867 (1.29) | 1.30 |
| SP5 | −1,159 (1.03) | 0.82 | 28,985 (1.18) | 4.58 | 552 (1.12) | 1.14 | 6,433 (1.24) | 3.24 |
| SP6 | 544 (1.36) | 1.08 | 3,313 (1.22) | 1.41 | 2,037 (1.04) | 1.51 | 2,069 (1.21) | 1.72 |
| SP8 | −948 (1.25) | 0.85 | 4,890 (1.49) | 1.60 | 2,601 (1.07) | 1.66 | 2,145 (1.21) | 1.70 |
| SP9 | 3,240 (1.17) | 1.50 | 4,074 (1.30) | 1.46 | 1,990 (1.10) | 0.91 | *2,279 (1.18) | 1.74 |
| SP10 | 2,218 (1.10) | 1.34 | *14,813 (1.44) | 2.83 | −79 (1.14) | 0.98 | 12,173 (1.05) | 4.96 |
| SP11 | 3,946 (1.20) | 1.61 | *11,811 (1.30) | 2.46 | −367 (1.20) | 0.91 | 3,343 (1.18) | 2.09 |
| V1E1 | 30,621 (1.11) | 5.73 | 957 (1.41) | 1.12 | −194 (1.17) | 0.95 | 862 (1.13) | 1.28 |
| V1E2 | 21,191 (1.27) | 4.27 | 1,252 (1.17) | 1.15 | 104 (1.20) | 1.03 | 2,155 (1.29) | 1.70 |
| V1E3 | 7,444 (1.09) | 2.15 | 1,910 (1.21) | 1.22 | −2,440 (1.11) | 0.38 | 792 (1.27) | 1.26 |
| V1E4 | 1,289 (1.07) | 1.20 | 25,568 (1.06) | 3.97 | −1,862 (1.13) | 0.53 | 1,111 (1.19) | 1.37 |
| V1E5 | 2,498 (1.16) | 1.39 | 7,186 (1.46) | 1.84 | −1,990 (1.30) | 0.50 | 4,669 (1.48) | 2.55 |
| V1E7 | −1,072 (1.16) | 0.83 | 13,155 (1.08) | 2.53 | −221 (1.39) | 0.94 | 2,885 (1.06) | 1.95 |
| V1E8 | 26,747 (1.11) | 5.13 | −2,009 (1.12) | 0.77 | 25,993 (1.07) | 7.56 | 1,928 (1.22) | 1.64 |
| V1E9 | 19,605 (1.28) | 3.76 | 26,721 (1.10) | 4.11 | 8,005 (1.39) | 2.31 | 8,196 (1.25) | 3.71 |
| V1E10 | 7,438 (1.07) | 1.43 | 27,183 (1.26) | 4.16 | 20,477 (1.20) | 5.92 | 1,149 (1.20) | 1.38 |
| Env. prot. | 106,677 (1.16) | 17.5 | 108,617 (1.10) | 13.6 | 91,367 (1.04) | 24.1 | 48,222 (1.10) | 17.0 |

DISCUSSION OF TABLE 2 a. The native envelope protein-immune lymph node cells were cultured with three different concentrations of peptides: 0.3 μM, 1.0 μM, and 3.0 μM. The [$^3$H]-TdR incorporation into the responding cells at highest concentration of the antigens (3 μM) is shown as Δ geometric mean (cpm), SEM, and stimulation indices (S.I.) (ratio of experimental mean to control mean without antigen).

b. The values underlined were highly statistically significant ($p<0.01$). Also these peptides stimulated significantly at lower antigen concentrations. These peptides were identified to be immunodominant for the corresponding mouse strains. The values with asterisks were statistically significant ($0.01<p<0.05$) only at the highest antigen concentration, 3.0 μM.

TABLE 3

Correlation of experimental immunodominance with α-helical amphipathicity prediction

A.

| | Type predicted | | |
|---|---|---|---|
| | α-helix | $3_{10}$ helix | non-helical |
| Tested sites | 10 | 3 | 4 |
| Immunodominant sites | 10 | 0 | 1 |
| % | 100 | 0 | 25 |

B.

| | Found immunogenic | Found non-immunogenic |
|---|---|---|
| Total sites | 11 | 6 |
| Predicted to be amphipathic alpha helix | 10 | 0 |

The peptides of the invention may be administered as immunogens in the usual carriers. The compositions for use as immunogens may contain adjuvants such as alum. Compositions containing VIE1, VIE8/SP4a and VIE10 are preferred. However, it is advisable that more than one of the epitopes taught herein be given. Compositions containing at least three epitopes are preferred.

Compositions may be administered in the usual manner. However, preferred routes of administration for vaccine use are subcutaneous, intradermal, or intramuscular routes.

The compositions of the invention can also be used as primers to elicit T-cell responses.

REFERENCES

1. Poiesz, B. J., F. W. Ruscetti, A. F. Gazdar, P. A. Bunn, J. D. Minna, and R. C. Gallo. 1980. Detection and isolation of type C retrovirus particles from fresh and cultured lymphocytes of a patient with cutaneous T-cell lymphoma. *Proc. Natl. Acad. Sci. U.S.A.* 77:7415–7419.
2. Yoshida, M., I. Miyoshi, and Y. Hinuma. 1982. Isolation and characterization of retrovirus from cell lines of human adult T-cell leukemia and its implication in the disease. *Proc. Natl. Aca. Sci. USA* 79:2031–2035.
3. Johnson, R. T., and J. C. McArthur. 1987. Myelopathies and Retroviral Infections. *Ann. Neurol* 21:113–116.
4. Gessain, A., J. C. Vernant, L. Maurs, F. Barin, O. Gout, A. Calender, and G. De-The. 1985. Antibodies to Human T-Lymphotropic virus Type-I in Patients with Tropical Spastic Paraparesis. *Lancet* 2:407–410.
5. Rodgers-Johnson, P., D. C. Gajdusek, O. St. C. Morgan, V. Zaninovic, P. S. Sarin, and D. S. Graham. 1985. HTLV-I and HTLV-III Antibodies and Tropical Spastic Paraparesis. *Lancet* 2:1247–1248.
6. Vernant, J. C., L. Maurs, A. Gessain, F. Barin, O. Gout, J. M. Delaporte, K. Sanhadji, G. Buisson, and G. De-The. 1987. Endemic Tropical Spastic Paraparesis Associated with Human T-Lymphotropic Virus Type I: A Clinical and Seroepidemiological Study of 25 Cases. *Ann. Neurol* 21:123–130.
7. Osame; M., K. Usuku, S. Izumo, N. Ijichi, H. Amitani, A. Igata, M. Matsumoto, and M. Tara. 1986. HTLV-I associated myelopathy, a new clinical entity. *Lancet* 1:1031–1032.
8. Usuku, K., S. Sonoda, M. Osame, S. Yashiki, K. Takahashi, M. Matsumoto, T. Sawada, K. Tsuji, M. Tara, and A. Igata. 1988. HLA haplotype-linked high immune responsiveness against HTLV-I in HTLV-I-associated myelopathy: comparison with adult T-cell leukemia/lymphoma. *Ann. Neurol* 23:S143–S150.
9. Lamb, J. R., D. D. Eckels, P. Lake, J. N. Woody, and N. Green. 1982. Human T cell clones recognize chemically synthesized peptides of influenza hemagglutinin. *Nature* 300:66–69.
10. Hurwitz, J. L., E. Heber-Katz, C. J. Hackett, and W. J. Gerhard. 1984. Characterization of the murine TH response to influenza virus hemagglutinin: evidence for three major specificities. *J. Immunol.* 133:3371–3377.
11. Cease, K. B., H. Margalit, J. L. Cornette, S. D. Putney, W. G. Robey, C. Ouyang, H. Z. Streicher, P. J. Fischinger, R. C. Gallo, C. Delisi, and J. A. Berzofsky. 1987. Helper T cell antigenic site identification in the AIDS virus gp120 envelope protein and induction of immunity in mice to the native protein using a 16-residue synthetic peptide. *Proc. Natl. Acad. Sci. USA* 84:4249–4253.
12. Berzofsky, J. A., A. Bensussan, K. B. Cease, J. F. Bourge, R. Cheynier, Z. Lurhuma, J.-J. Salaün, R. C. Gallo, G. M. Shearer, and D. Zagury. 1988. Antigenic peptides recognized by T lymphocytes from AIDS viral envelope-immune humans. *Nature* 334:706–708.
13. Good, M. F., W. L. Maloy, M. N. Lunde, H. Margalit, J. L. Cornette, G. L. Smith, B. Moss, L. H. Miller, and J. A. Berzofsky. 1987. Construction of a synthetic immunogen: use of a new T-helper epitope on malaria circumsporozoite protein. *Science* 235:1059–1062.
14. Good, M. F., D. Pombo, I. A. Quakyi, E. M. Riley, R. A. Houghten, A. Menon, D. W. Alling, J. A. Berzofsky, and L. H. Miller. 1988. Human T cell recognition of the circumsporozoite protein of *Plasmodium falciparum.* Immunodominant T cell domains map to the polymorphic regions of the molecule. *Proc. Natl. Acad. Sci. USA* 85:1199–1203.
15. Dontfraid, F., M. A. Cochran, D. Pombo, J. D. Knell, I. Quakyi, S. Kumar, R. A. Houghten, J. A. Berzofsky, L. H. Miller, and M. F. Good. 1988. Human and murine CD4 T-cell epitopes map to the same region of the malaria circumsporozoite protein: Limited immunogenicity of sporozoites and cirumsporozoite protein. *Mol. Bid. Med.*
16. Sinigaglia, F., M. Guttinger, J. Kilgus, D. M. Doran, H. Matile, H. Etlinger, A. Trzeciak, D. Gillessen, and J. R. L. Pink. 1988. A malaria T-cell epitope recognized in association with most mouse and human MHC class II molecules. *Nature* 336:778–780.
17. Delisi, C., and J. A. Berzofsky. 1985. T cell antigenic sites tend to be amphipathic structures. *Proc. Natl. Acad. Sci. U.S.A.* 82:7048–7052.
18. Margalit, H., J. L. Spouge, J. L. Cornette, K. Cease, C. Delisi, and J. A. Berzofsky. 1987. Prediction of immunodominant helper T-cell antigenic sites from the primary sequence. *J. Immunol.* 138:2213–2229.

19. Palker, T. J., M. E. Clark, M. G. Sarngadharan, and T. J. Matthews. 1987. Purification of envelope glycoproteins of human T cell lymphotropic virus type I (HTLV-I) by affinity chromatography. *J. Virol. Methods* 18:243.

20. Spouge, J. L., H. R. Guy, J. L. Cornette, H. Margalit, K. Cease, J. A. Berzofsky, and C. Delisi. 1987. Strong conformational propensities enhance T-cell antigenicity. *J. Immunol.* 138:204–212.

21. Berzofsky, J. A., K. B. Cease, J. L. Cornette, J. L. Spouge, H. Margalit, I. J. Berkower, M. F. Good, L. H. Miller, and C. Delisi. 1987. Protein antigenic structures recognized by T cells: Potential applications to vaccine design. *Immunol. Rev.* 98:9–52.

22. Cornette, J. L., H. Margalit, C. Delisi, and J. A. Berzofsky. 1989. Concepts and methods in the identification of T cell epitopes and their use in the construction of synthetic vaccines. *Methods in Enzymol.*

23. Kyte, J., and R. F. Doolittle. 1982. A simple method for displaying the hydrophilic character of a protein. *J. Mol. Biol.* 157:105.

24. Palker, T. J., M. E. Tanner, R. M. Scearce, R. D. Streilein, M. E. Clark, and B. F. Haynes. 1989. Mapping of immunogenic regions of human T cell leukemia virus type I (HTLV-I) gp46 and gp21 envelope glycoproteins with env-encoded synthetic peptides and a monoclonal antibody to gp46. *J. Immunol.* 142:971–978.

25. Merrifield, R. B. 1965. Automated synthesis of peptides. *Science* 150:178–185.

26. Stewart, J. M., and J. D. Young. 1984. *Solid Phase Peptide Synthesis.* Pierce Chemical Company, Rockford, Ill., 27. Corradin, G., H. M. Etlinger, and J. M. Chiller. 1977. Lymphocyte specificity in protein antigens. I. Characterization of the antigen-induced in vitro T cell-dependent proliferative response with lymph node cells from primed mice. *J. Immunol.* 119:1048.

28. Seiki, M., S. Hattori, and M. Yoshida. 1982. Human adult T-cell leukemia virus: Molecular cloning of the provirus DNA and the unique terminal structure. *Proc. Natl. Acad. Sci. USA* 79:6899–6902.

29. Takahashi, H., J. Cohen, A. Hosmalin, K. B. Cease, R. Houghten, J. Cornette, C. Delisi, B. Moss, R. N. Germain, and J. A. Berzofsky. 1988. An immunodominant epitope of the HIV gp160 envelope glycoprotein recognized by class I MHC molecule-restricted murine cytotoxic T lymphocytes. *Proc. Natl. Acad. Sci. USA* 85:3105 –3109.

30. Thomas, D. B., J. J. Skehel, K. H. G. Mills, and C. M. Graham. 1987. A single amino acid substitution in influenza haemagglutinin abrogates recognition by a monoclonal antibody and a spectrum of subtype-specific L3T4+ T cell clones. *Eur. J. Immunol.* 17:133–136.

31. Palker, T. J., T. J. Matthews, A. Langlois, M. E. Tanner, M. E. Martin, R. M. Scearce, J. E. Kim, J. A. Berzofsky, D. P. Bolognesi, and B. F. Haynes. 1989. Polyvalent human immunodeficiency virus synthetic immunogen comprised of envelope gp120T helper cell sites and B cell neutralization epitopes. *J. Immunol.* 142: in press.

32. Malik, K. T. A., J. Evan, and A. Karpas. 1988. Molecular cloning and complete nucleotide sequence of an adult T cell leukaemia virus/human T cell leukaemia virus type I (ATLV/HTLV-I) isolate of Caribbean origin: relationship to other members of the ATLV/HTLV-I subgroup. *J. Gen. Virol.* 69:1695.

We claim:

1. A peptide consisting of amino acids having a sequence selected from the group consisting of SGKSLLHEVDKDISQLTQAIVK, DISQLTQAIVKNHKNLLK, VKNHKNLLKIAQYAAQN, EQGGLCKALQEQCRF, LAGPCILRQLRHLPSRVR, GGYYSASYSDPCSLK, TLPFNWTHCFDPQIQAIVS, and FTQEVSRLNINLHFSK and LPHSNLDHILEPSIPWKSK.

2. A peptide consisting of amino acids having a sequence selected from the group consisting of EQGGLCKALQEQCRF, LAGPCILRQLRHLPSRVR, GGYYSASYSDPCSLK, LPHSNLDHILEPSIPWKSK and TLPFNWTHCFDPQIQAIVS.

3. A peptide consisting of amino acids having a sequence selected from the group consisting of SGKSLLHEVDKDISQLTQAIVK, DISQLTQAIVKNHKNLLK, VKNHKNLLKIAQYAAQN, and FTQEVSRLNINLHFSK.

4. A peptide of claim 3, wherein said amino acid sequence is FTQEVSRLNINLHFSK.

5. A peptide of claim 3, wherein said amino acid sequence is SGKSLLHEVDKDISQLTQAIVK.

6. A peptide of claim 3, wherein said amino acid sequence is DISQLTQAIVKNHKNLLK.

7. A peptide of claim 3, wherein said amino acid sequence is VKNHKNLLKIAQYAAQN.

8. A peptide consisting essentially of:

i) a peptide consisting of amino acids having a sequence selected from the group consisting of EQGGLCKALQEQCRF, LAGPCILRQLRHLPSRVR, GGYYSASYSDPCSLK, LPHSNLDHILEPSIPWKSK and TLPFNWTHCFDPQIQAIVS and ii) a peptide providing an epitope that stimulates a helper T-cell or lymph node cell proliferative response;

wherein said peptide ii) is covalently attached to said peptide i).

9. A peptide consisting essentially of:

i) a peptide consisting of amino acids having a sequence selected from the group consisting of SGKSLLHEVDKDISQLTQAIVK, DISQLTQAIVKNHKNLLK, VKNHKNLLKIAQYAAQN, and FTQEVSRLNINLHFSK, and ii) a peptide providing an epitope that stimulates a helper T-cell or lymph node cell proliferative response;

wherein said peptide ii) is covalently attached to said peptide i).

10. A composition comprising a plurality of peptides consisting of amino acids having a sequence selected from the group consisting of EQGGLCKALQEQCRF, LAGPCILRQLRHLPSRVR, GGYYSASYSDPCSLK, LPHSNLDHILEPSIPWKSK, TLPFNWTHCFDPQIQAIVS, SGKSLLHEVDKDISQLTQAIVK, DISQLTQAIVKNHKNLLK, VKNHKNLLKIAQYAAQN, and FTQEVSRLNINLHFSK, wherein said plurality of peptides is conjugated one to another.

11. A composition comprising a plurality of peptides consisting of amino acids having a sequence selected from the group consisting of SGKSLLHEVDKDISQLTQAIVK, DISQLTQAIVKNHKNLLK, VKNHKNLLKIAQYAAQN, and FTQEVSRLNINLHFSK, wherein said plurality of peptides is conjugated one to another.

12. A composition comprising a peptide according to claim 2 and a carrier or adjuvant.

13. A composition comprising a peptide according to claim 3 and a carrier or adjuvant.

14. A composition comprising a peptide according to claim 9 and a carrier or adjuvant.

15. A composition according to claim 10, further comprising a carrier or adjuvant.

16. A composition according to claim 11, further comprising a carrier or adjuvant.

17. A peptide consisting essentially of:

i) a peptide consisting of amino acids having a sequence selected from the group consisting of EQGGLCKALQEQCRF, LAGPCILRQLRHLPSRVR, GGYYSASYSDPCSLK, LPHSNLDHILEPSIPWKSK and TLPFNWTHCFDPQIQAIVS and ii) a peptide providing an epitope that stimulates a cytotoxic T lymphocyte response;

wherein said peptide ii) is covalently attached to said peptide i).

18. A peptide consisting essentially of:

i) a peptide consisting of amino acids having a sequence selected from the group consisting of SGKSLLHEVDKDISQLTQAIVK, DISQLTQAIVKNHKNLLK, VKNHKNLLKIAQYAAQN, and FTQEVSRLNINLHFSK; and ii) a peptide providing an epitope that stimulates a cytotoxic T lymphocyte response;

wherein said peptide ii) is covalently attached to said peptide i).

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS:
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..15
( D ) OTHER INFORMATION: /label=peptide_SP1

( x i ) SEQUENCE DESCRIPTION: SEQ ID NO:1:

Val Ser Ser Tyr His Ser Lys Pro Cys Asn Pro Ala Gln Pro Val
1 5 10 15

( 2 ) INFORMATION FOR SEQ ID NO:2:

( i ) SEQUENCE CHARACTERISTICS:
( A ) LENGTH: 23 amino acids

-continued (B) TYPE: amino acid
(C) STRANDEDNESS: Not Relevant
(D) TOPOLOGY: Not Relevant (ii) MOLECULE TYPE: peptide (iii) HYPOTHETICAL: NO (v) FRAGMENT TYPE: internal (vi) ORIGINAL SOURCE:
(A) ORGANISM: htlv-I (ix) FEATURE:
(A) NAME/KEY: Peptide
(B) LOCATION: 1..23
(D) OTHER INFORMATION: /label=peptide_sp2

(xi) SEQUENCE DESCRIPTION: SEQ ID NO:2:

```
Cys Pro His Trp Thr Lys Lys Pro Asn Arg Asn Gly Gly Gly Tyr Tyr
1               5                   10                  15

Ser Ala Ser Tyr Ser Asp Pro
            20
```

(2) INFORMATION FOR SEQ ID NO:3:

(i) SEQUENCE CHARACTERISTICS:
(A) LENGTH: 16 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (v) FRAGMENT TYPE: internal (vi) ORIGINAL SOURCE:
(A) ORGANISM: htlv-I (ix) FEATURE:
(A) NAME/KEY: Peptide
(B) LOCATION: 1..16
(D) OTHER INFORMATION: /label=peptide_sp3

(xi) SEQUENCE DESCRIPTION: SEQ ID NO:3:

```
Cys Leu Asn Thr Glu Pro Ser Gln Leu Pro Pro Thr Ala Pro Pro Tyr
1               5                   10                  15
```

(2) INFORMATION FOR SEQ ID NO:4:

(i) SEQUENCE CHARACTERISTICS:
(A) LENGTH: 22 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (v) FRAGMENT TYPE: internal (vi) ORIGINAL SOURCE:
(A) ORGANISM: htlv-I (ix) FEATURE:
(A) NAME/KEY: Peptide
(B) LOCATION: 1..22
(D) OTHER INFORMATION: /label=peptide_sp4a (xi) SEQUENCE DESCRIPTION: SEQ ID NO:4:

```
Cys Leu Leu Pro His Ser Asn Leu Asp His Ile Leu Glu Pro Ser Ile
```

-continued 1 5 10 15

Pro Trp Lys Ser Lys Tyr
20

( 2 ) INFORMATION FOR SEQ ID NO:5:

( i ) SEQUENCE CHARACTERISTICS:
( A ) LENGTH: 14 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..14
( D ) OTHER INFORMATION: /label=peptide_sp5

( x i ) SEQUENCE DESCRIPTION: SEQ ID NO:5:

Tyr Leu Pro Phe Asn Trp Thr His Cys Phe Asp Pro Gln Cys
1 5 10

( 2 ) INFORMATION FOR SEQ ID NO:6:

( i ) SEQUENCE CHARACTERISTICS:
( A ) LENGTH: 18 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..18
( D ) OTHER INFORMATION: /label=peptide_sp6

( x i ) SEQUENCE DESCRIPTION: SEQ ID NO:6:

Cys Pro Pro Phe Ser Leu Ser Pro Val Pro Thr Leu Gly Ser Arg Ser
1 5 10 15

Arg Arg ( 2 ) INFORMATION FOR SEQ ID NO:7:

( i ) SEQUENCE CHARACTERISTICS:
( A ) LENGTH: 16 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I -continued ( i x ) FEATURE:
( A ) NAME/KEY: Peptide
( B ) LOCATION: 1..16
( D ) OTHER INFORMATION: /label=peptide_sp8

( x i ) SEQUENCE DESCRIPTION: SEQ ID NO:7:

Cys Arg Phe Pro Asn Ile Thr Asn Ser His Val Pro Ile Leu Gln Glu
1 5 10 15

( 2 ) INFORMATION FOR SEQ ID NO:8:

( i ) SEQUENCE CHARACTERISTICS:
( A ) LENGTH: 13 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..13
( D ) OTHER INFORMATION: /label=peptide_sp9

( x i ) SEQUENCE DESCRIPTION: SEQ ID NO:8:

Cys Pro Ile Leu Gln Glu Arg Pro Pro Leu Glu Asn Arg
1 5 10

( 2 ) INFORMATION FOR SEQ ID NO:9:

( i ) SEQUENCE CHARACTERISTICS:
( A ) LENGTH: 19 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..19
( D ) OTHER INFORMATION: /label=peptide_sp10

( x i ) SEQUENCE DESCRIPTION: SEQ ID NO:9:

Cys Ile Leu Arg Gln Leu Arg His Leu Pro Ser Arg Val Arg Tyr Pro
1 5 10 15

His Tyr Ser ( 2 ) INFORMATION FOR SEQ ID NO:10:

( i ) SEQUENCE CHARACTERISTICS:
( A ) LENGTH: 15 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..15
( D ) OTHER INFORMATION: /label=peptide_sp11

( x i ) SEQUENCE DESCRIPTION: SEQ ID NO:10:

Cys Arg Tyr Pro His Tyr Ser Leu Ile Lys Pro Glu Ser Ser Leu
1 5 10 15

( 2 ) INFORMATION FOR SEQ ID NO:11:

( i ) SEQUENCE CHARACTERISTICS:
( A ) LENGTH: 22 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..22
( D ) OTHER INFORMATION: /label=peptide_v1e1

( x i ) SEQUENCE DESCRIPTION: SEQ ID NO:11:

Ser Gly Lys Ser Leu Leu His Glu Val Asp Lys Asp Ile Ser Gln Leu
1 5 10 15

Thr Gln Ala Ile Val Lys
20

( 2 ) INFORMATION FOR SEQ ID NO:12:

( i ) SEQUENCE CHARACTERISTICS:
( A ) LENGTH: 18 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..18
( D ) OTHER INFORMATION: /label=peptide_v1e2

( x i ) SEQUENCE DESCRIPTION: SEQ ID NO:12:

Asp Ile Ser Gln Leu Thr Gln Ala Ile Val Lys Asn His Lys Asn Leu
1 5 10 15

Leu Lys ( 2 ) INFORMATION FOR SEQ ID NO:13:

( i ) SEQUENCE CHARACTERISTICS:
( A ) LENGTH: 17 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..17
( D ) OTHER INFORMATION: /label=peptide_v1e3

( x i ) SEQUENCE DESCRIPTION: SEQ ID NO:13:

Val Lys Asn His Lys Asn Leu Leu Lys Ile Ala Gln Tyr Ala Ala Gln
1 5 10 15

Asn ( 2 ) INFORMATION FOR SEQ ID NO:14:

( i ) SEQUENCE CHARACTERISTICS:
( A ) LENGTH: 15 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..15
( D ) OTHER INFORMATION: /label=peptide_v1e4

( x i ) SEQUENCE DESCRIPTION: SEQ ID NO:14:

Glu Gln Gly Gly Leu Cys Lys Ala Leu Gln Glu Gln Cys Arg Phe
1 5 10 15

( 2 ) INFORMATION FOR SEQ ID NO:15:

( i ) SEQUENCE CHARACTERISTICS:
( A ) LENGTH: 18 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..18
( D ) OTHER INFORMATION: /label=peptide_v1e5

( x i ) SEQUENCE DESCRIPTION: SEQ ID NO:15:

-continued

Leu Ala Gly Pro Cys Ile Leu Arg Gln Leu Arg His Leu Pro Ser Arg
1 5 10 15

Val Arg ( 2 ) INFORMATION FOR SEQ ID NO:16:

( i ) SEQUENCE CHARACTERISTICS:
( A ) LENGTH: 15 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..15
( D ) OTHER INFORMATION: /label=peptide_v1e7

( x i ) SEQUENCE DESCRIPTION: SEQ ID NO:16:

Gly Gly Tyr Tyr Ser Ala Ser Tyr Ser Asp Pro Cys Ser Leu Lys
1 5 10 15

( 2 ) INFORMATION FOR SEQ ID NO:17:

( i ) SEQUENCE CHARACTERISTICS:
( A ) LENGTH: 19 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..19
( D ) OTHER INFORMATION: /label=peptide_v1e8

( x i ) SEQUENCE DESCRIPTION: SEQ ID NO:17:

Leu Pro His Ser Asn Leu Asp His Ile Leu Glu Pro Ser Ile Pro Trp
1 5 10 15

Lys Ser Lys ( 2 ) INFORMATION FOR SEQ ID NO:18:

( i ) SEQUENCE CHARACTERISTICS:
( A ) LENGTH: 19 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:

-continued ( A ) ORGANISM: htlv-I ( i x ) FEATURE:
( A ) NAME/KEY: Peptide
( B ) LOCATION: 1..19
( D ) OTHER INFORMATION: /label=peptide_v1e9

( x i ) SEQUENCE DESCRIPTION: SEQ ID NO:18:

Thr Leu Pro Phe Asn Trp Thr His Cys Phe Asp Pro Gln Ile Gln Ala
1 5 10 15

Ile Val Ser ( 2 ) INFORMATION FOR SEQ ID NO:19:

( i ) SEQUENCE CHARACTERISTICS:
( A ) LENGTH: 16 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: htlv-I ( i x ) FEATURE:
( A ) NAME/KEY: Peptide
( B ) LOCATION: 1..16
( D ) OTHER INFORMATION: /label=peptide_v1e10

( x i ) SEQUENCE DESCRIPTION: SEQ ID NO:19:

Phe Thr Gln Glu Val Ser Arg Leu Asn Ile Asn Leu His Phe Ser Lys
1 5 10 15